(12) United States Patent
Herron et al.

(10) Patent No.: US 10,365,215 B2
(45) Date of Patent: Jul. 30, 2019

(54) METHOD AND SYSTEM FOR ANALYZING AN EARTH SAMPLE OF A GEOLOGICAL FORMATION

(71) Applicant: SCHLUMBERGER TECHNOLOGY CORPORATION, Sugar Land, TX (US)

(72) Inventors: Michael Herron, Ridgefield, CT (US); Mary Ellen Loan, Quincy, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/197,885

(22) Filed: Jun. 30, 2016

(65) Prior Publication Data

US 2018/0003629 A1    Jan. 4, 2018

(51) Int. Cl.
| | |
|---|---|
| *G01N 33/24* | (2006.01) |
| *G01N 21/3563* | (2014.01) |
| *G01N 21/47* | (2006.01) |
| *G01N 21/35* | (2014.01) |

(52) U.S. Cl.
CPC ....... *G01N 21/3563* (2013.01); *G01N 21/474* (2013.01); *G01N 33/24* (2013.01); *G01N 2021/3595* (2013.01); *G01N 2021/4764* (2013.01)

(58) Field of Classification Search
CPC ............. G01N 21/3563; G01N 21/359; G01N 21/314; G01N 21/3504; G01J 3/36
See application file for complete search history.

(56) References Cited

U.S. PATENT DOCUMENTS

2013/0046469 A1* 2/2013 Herron ............... G01N 21/3563
                                                              702/2
2013/0269933 A1  10/2013 Pomerantz et al.

OTHER PUBLICATIONS

Charsky et al., Quantitative analysis of kerogen content and mineralogy in shale cuttings by Diffuse Reflectance Infrared Fourier Transform Spectroscopy, International Symposium of the Society of Core Analysts held in Aberdeen, Scotland, UK, 27-30, 2012, 12 pages.
Herron, Michael M. et al., Clay Typing, Mineralogy, Kerogen Content and Kerogen Characterization from Drifts Analysis of Cuttings or Core, Unconventional Resources Technology Conference, Denver, Colorado, USA, Aug. 25-27, 2014, 11 pages.
(Continued)

*Primary Examiner* — David P Porta
*Assistant Examiner* — Mamadou Faye

(57) ABSTRACT

The disclosure relates to a method for analyzing earth samples of a geological formation, comprising:
  performing a Fourier Transform InfraRed (FTIR) spectrometry measurement on an earth sample collected in the formation by:
    Irradiating the sample with infrared energy
    Measuring a spectrum representative of the infrared energy absorbed by the earth sample,
  analyzing the measured spectrum and obtaining from the analyzed measured spectrum a reconstructed spectrum corresponding to a combination of a plurality of standard spectra representative of elements contained in the earth sample,
  based on the measured spectrum and on the reconstructed spectrum, detecting a tar layer in the geological formation.

17 Claims, 5 Drawing Sheets

(56) References Cited

OTHER PUBLICATIONS

Herron, Susan et al., Application and Quality Control of Core Data for the Development and Validation of Elemental Spectroscopy Log Interpretation, Society of Petrophysicists and Well Log Analysts (SPWLA) 55th Annual Logging Symposium held in Abu Dhabi, United Arab Emirates, May 18-22, 2014, 23 pages.

* cited by examiner

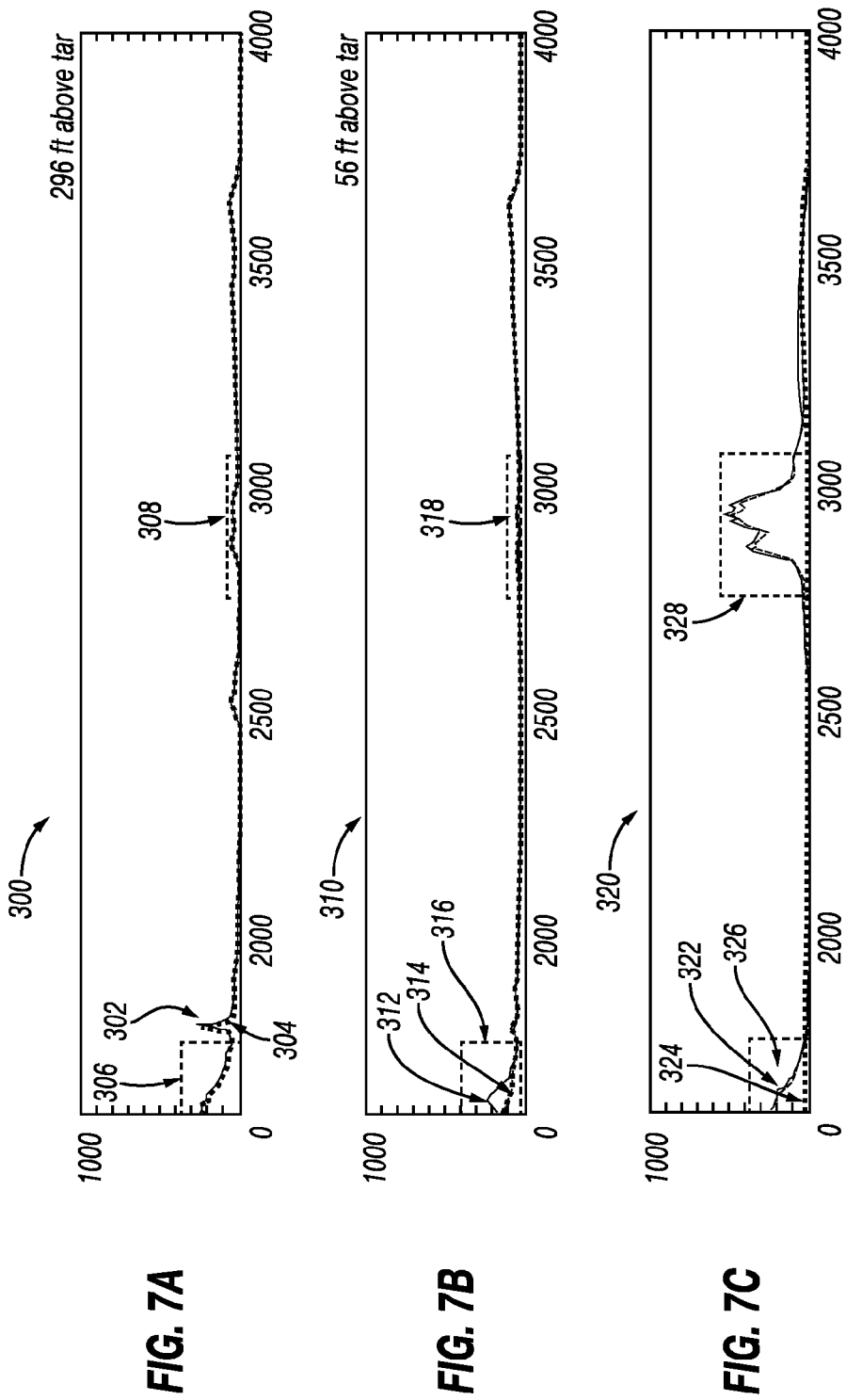

METHOD AND SYSTEM FOR ANALYZING AN EARTH SAMPLE OF A GEOLOGICAL FORMATION

BACKGROUND

The disclosure relates to a method and a system for analyzing an earth sample of a geological formation.

It is already known in the art to collect earth samples from the formation, such as drill cuttings collected during the drilling of the borehole, and to analyze these samples in order to obtain information relative to the formation.

It is for example known to submit an earth sample to FTIR (Fourier Transform Infrared) spectroscopy, such as DRIFTS (Diffuse Reflectance Fourier Transform Infrared Spectroscopy), in order to derive from the measurement a characterization of the formation, such as the mineralogy of the formation or the TOC (total organic content), as already disclosed in the published application US20130046469 of the Applicants.

SUMMARY

The disclosure relates to deriving other helpful indicators from a FTIR measurement.

In a first embodiment, the disclosure relates to a method for analyzing at least an earth sample of a geological formation, comprising Performing a Fourier Transform InfraRed (FTIR) spectrometry measurement on an earth sample collected in the formation by irradiating the sample with infrared energy and measuring a spectrum representative of the infrared energy absorbed by the sample, analyzing the measured spectrum and obtaining from the analyzed measured spectrum a reconstructed spectrum corresponding to a combination of a plurality of standard spectra representative of elements contained in the earth sample, and, based on the measured spectrum and on the reconstructed spectrum, detecting a tar layer in the geological formation.

A tar layer, which is a layer constituted at least in part of a heavy hydrocarbon, may generate problems during the drilling of the borehole in the geological formation. Indeed, when the drill bit encounters a tar layer, especially when this tar layer is not consolidated, it may get stuck or twisted off. Detecting the tar layer as soon as possible may help facilitate the drilling process.

The method may detect a tar layer ahead of the drill bit, by detecting and locating a tar layer based on earth samples situated in the formation not only in the tar layer but also above the tar layer, for instance 0 to 200 feet above the tar layer.

In a second embodiment, the disclosure relates to a system for analyzing an earth sample of a geological formation comprising a Fourier Transform InfraRed (FTIR) spectrometry measurement apparatus for irradiating an earth sample with infrared energy and measuring a spectrum representative of the infrared energy absorbed by the earth sample, and a calculator for analyzing the measured spectrum and obtaining from the analyzed measured spectrum a reconstructed spectrum corresponding to a combination of a plurality of standard spectra representative of elements contained in the earth sample, and, based the measured spectrum and on the reconstructed spectrum, detecting a tar layer in the geological formation In a third embodiment, the disclosure relates to a computer program, comprising machine-readable instructions for receiving a measured spectrum obtained from a Fourier Transform InfraRed (FTIR) spectrometry measurement on an earth sample of a geological formation, analyzing the measured spectrum and obtaining from the analyzed measured spectrum a reconstructed spectrum corresponding to a combination of a plurality of standard spectra representative of elements contained in the earth sample, and, based on the measured spectrum and the reconstructed spectrum, detecting a tar layer in the geological formation.

BRIEF DESCRIPTION OF THE DRAWINGS

Various aspects of this disclosure may be better understood upon reading the following detailed description and upon reference to the drawings in which:

FIG. 7A-7C are a plot of spectrograms obtained from earth samples coming from different depths of a same well drilled in a formation containing a tar layer.

DETAILED DESCRIPTION

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. In the specification, "upstream" and "downstream" are used in reference with the flow of the drilling mud.

The disclosure relates to characterize the formation via a cuttings analysis method and system. As it is well-known, a geological formation is constituted of several superimposed layers having different chemical compositions and properties, such as mechanical properties. Depending on the type of layers, difficulties may arise during the drilling of the borehole. For instance, drilling a tar layer, the drill bit may get stuck. Avoiding tar layers during drilling would significantly facilitate the drilling of the wellbore. Further, if the hydrocarbon in a hydrocarbon-rich formation is known to be tar, and therefore uneconomical to produce, this is also useful information to get the information as soon as possible.

The disclosure relates to a method for analyzing an earth sample from the formation for detecting a tar layer as soon as possible, in particular ahead of the drill bit.

Figure 1:
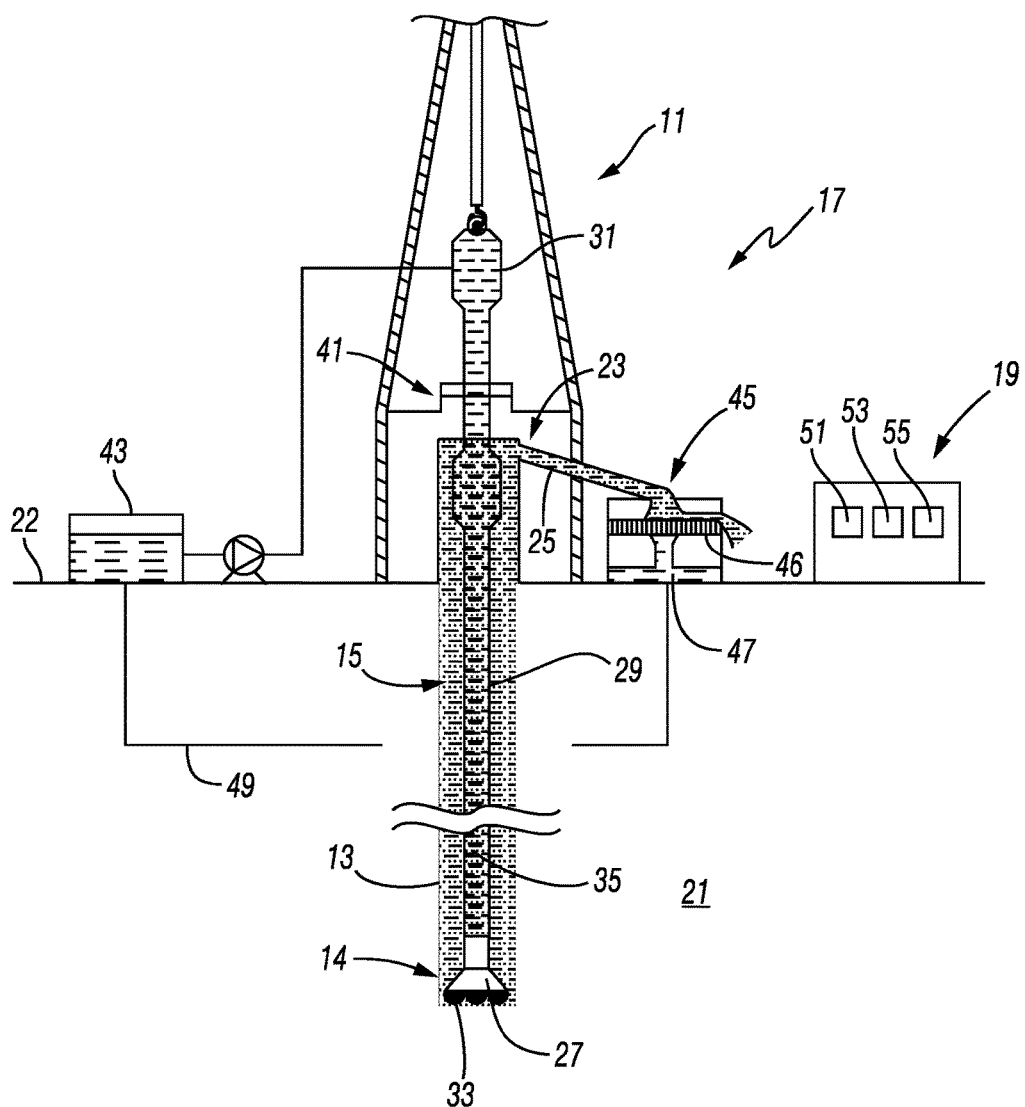
FIG. 1 is a schematic view of a system for analyzing an earth sample according to an embodiment of the disclosure.

FIG. 1 shows a system 10 for extracting drill cuttings from a geological formation while drilling a borehole in the formation.

The system 10 is used for example in a drilling installation 11 for a fluid production well, such as a hydrocarbon production well. As illustrated in FIG. 1, the installation 11 comprises a rotary drilling tool 15 drilling a cavity or borehole 14 in the ground, a surface installation 17, where drilling pipes are placed in the cavity 14, and a cuttings analysis device 19. A well 13 delimiting the cavity 14 is formed in the geological formation 21 by the rotary drilling tool 15. At the surface 22, a well head 23 having a discharge pipe 25 closes the well 13.

The drilling tool 15 comprises a drilling head 27, a drill string 29 and a liquid injection head 31. The drilling head 27 comprises a drill bit 33 for drilling through the rocks and/or sediments of the substratum 21, the drilling operation producing solid drilling residues or "cuttings". The drilling head 27 is mounted on the lower portion of the drill string 29 and is positioned at the bottom of the drilling pipe 13. The drill string 29 comprises a set of hollow drilling pipes. These pipes delimit an internal space 35 which makes it possible to bring a drilling fluid from the surface 22 to the drilling head 27. To this end, the liquid injection head 31 is screwed onto the upper portion of the drill string 29. The drilling fluid is in particular a drilling mud, in particular a water-based or oil-based drilling mud.

The surface installation 17 comprises a support frame 41 for supporting the drilling tool and driving it in rotation, an injector 43 for injecting the drilling liquid, and a shale shaker 45, for receiving and treating the effluent emerging from the well. The injector 43 is hydraulically connected to the injection head 31 in order to introduce and circulate the drilling fluid in the inner space 35 of the drill string 29. The shale shaker 45 collects the drilling fluid charged with cuttings which emerges from the discharge pipe 25. The shale shaker 45 is equipped with sieves 46 to allow the separation of the solid drilling residues or cuttings, from the drilling mud. The shale shaker 45 also comprises a tank 47 located under the sieves 46 to 5 recover the drilling mud deprived of cuttings.

The surface installation 17 further comprises a recirculation duct 49 connecting the recovery tank 47 to the injection means 43 to re-circulate the mud collected in the tank 47 to the injection means 43.

The cuttings analysis assembly 19 is intended for conditioning a rock sample composed of cuttings contained in the drilling mud emerging from the discharge pipe 25, and to analyze the cuttings of the rock sample. The cuttings are in particular collected at the sieves 46 of the shale shaker 45. These cuttings are made of small pieces of rocks and/or sediments which are generated of the cavity 14.

As shown in FIG. 1, the cuttings analysis assembly 19 comprises a sample preparation unit 53, and an analysis unit 55. The cuttings analysis assembly comprise as well a calculator 51.

The sample preparation unit 53 and the sample analysis unit 55 may be located at the well site, in a specifically equipped cabin in the vicinity of the drilling site or at the shale shaker, an automated process enabling the cuttings to pass sequentially in sample preparation unit 53 and analysis unit 55. Alternately, they may be located remotely from the well site in a lab. The calculator 51 may also be located on site or remotely, and be connected directly or via a network to the analysis unit 55. It can be in particular located at the same location or at a different location than the analysis unit.

The sample preparation unit 53, may comprise one or several of the following: at least one sieve for collecting the cuttings, at least a cleaning device, for rinsing the cuttings, at least an instrument for crushing the cuttings. A specific sample preparation method for preparing the cuttings that may be followed is described in patent application US 2013-0269933 from the Applicants. However, any appropriate preparation method may also be in the scope of the disclosure. The sample preparation may also be optional.

The sample preparation unit 53 may also comprise a tagging device for associating the collected drill cuttings with a particular collecting time and/or depth in the borehole. The collecting time is related to the depth at which the cuttings were collected from the formation and may be determined in view of the lag time, which is a well-known parameter that may be calculated in any appropriate way.

Figure 2:
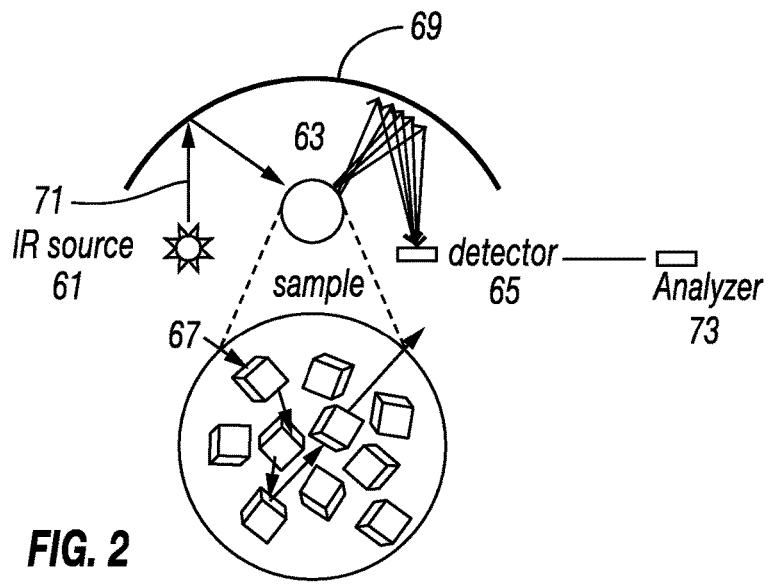
FIG. 2 is a schematic view of a FTIR analyzer of the system of FIG. 1 according to an embodiment of the disclosure.

The analysis device comprises a FTIR spectrometer, and in particular a DRIFTS spectrometer 60 (Diffuse Reflectance Infrared Fourier Transform Spectrometer). The spectrometer may comprise as depicted in FIG. 2, a source 61 of infrared radiation. Source 61 emits radiation beam 71 which is directed to spherical mirror 69 which, in turn, directs source 61 to sample 63. When the infrared light source 61 is directed at a sample 63, the infrared beam 67 is absorbed, specularly reflected, diffusely reflected, or transmitted through part of the sample. The reflected energy is captured by spherical mirror 69 and reflected down to detector 65. The detector 65 then collects the diffusely reflected light which is measured as a function of wavenumber. Each fundamental molecular vibration corresponds to a specific absorbance band, therefore, the sample components can be extracted by analyzing the DRIFTS spectrum. The FTIR spectrometer may be any appropriate FTIR spectrometer (for instance an FTIR apparatus for measuring a transmitted spectrum) enabling to measure the absorbance of the sample and not only a DRIFTS spectrometer. The analysis device may also comprise additional measurement devices, such as an x-ray fluorescence (XRF) device, an x-ray diffraction (XRD) device, organic carbon analyzer, or other apparatuses as known to those skilled in the art for characterizing rock samples The calculator 51 comprises for instance a computer comprising a processor able to execute machine-readable instructions and a storage unit, comprising a volatile and/or non-volatile memory, able to store the programs containing machine-readable instructions and/or a database, such as a standard spectra database that may be used for analyzing the measured spectrum obtained from the FTIR spectrometer.

Figure 3:
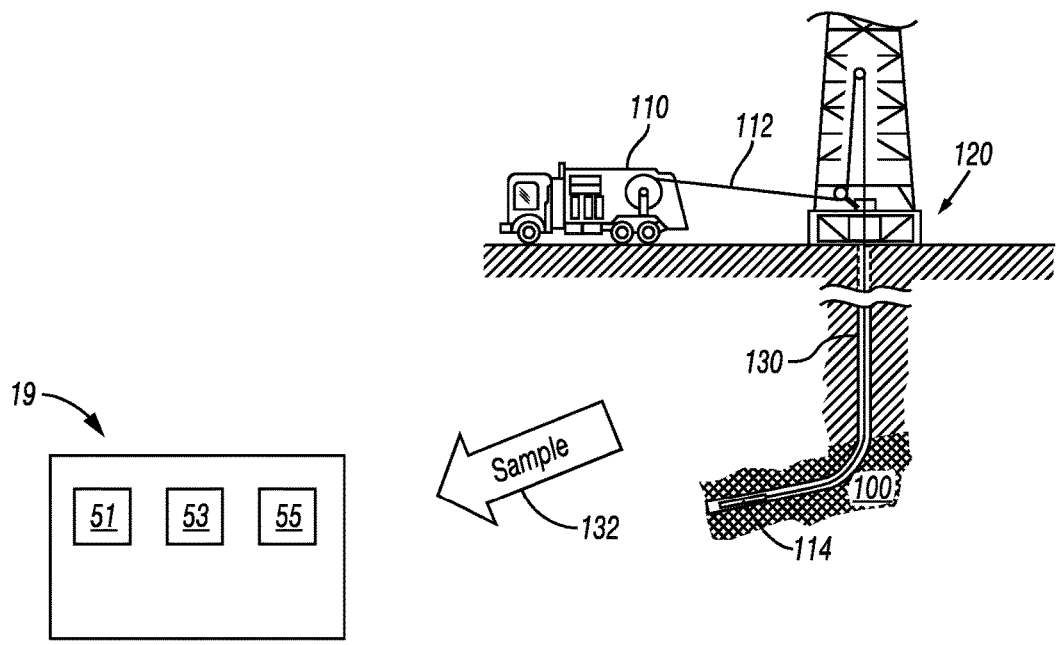
FIG. 3 is a schematic view of a system for analyzing the earth sample according to another embodiment of the disclosure.

The system described in relationship with FIG. 1 is a system in which the earth sample is constituted of drill cuttings collected while drilling, at the surface. However, the earth sample may be collected by any appropriate way, for instance directly in the formation via a sampling tool FIG. 3 shows a sampling tool being deployed in a wellbore and an analysis facility, according to some embodiments of the disclosure. In a non-limiting example the sampling tool is a core sampling tool. Wireline truck 110 is deploying wireline cable 112 into well 130 via well head 120. Wireline tool 114 is disposed on the end of the cable 112 in an unconventional subterranean formation (100). Tool 114 includes a sampling tool as shown, in a non-limiting example, a core sampling tool. Although a wireline sampling tool is shown, according to other embodiments, other types of sampling tools are used such as while drilling and/or coiled tubing conveyed tools. Samples 132 are retrieved at the surface from the tool 114 and transported to an analysis facility 150, that may include the cuttings analysis assembly already described hereinabove. Note that the analysis facility 150 can be located at the wellsite (which can be onshore or offshore) or it can be located remotely from the wellsite.

Figure 4:
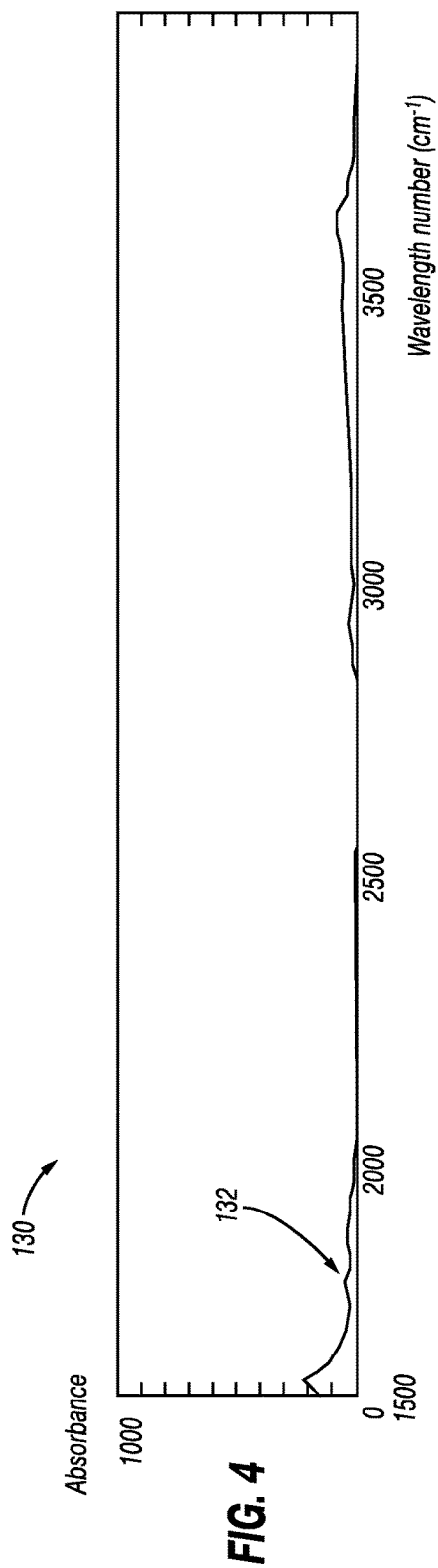
FIG. 4 is a spectrogram of a measured spectrum obtained by the FTIR analyzer of FIG. 2.

FIG. 4 shows a spectrogram 130 of an absorbance spectrum 132 of an earth sample measured via the FTIR analysis device 55. As can be seen the spectrum gives the absorbance of the sample for a wide number of wavelengths.

Figure 5C:
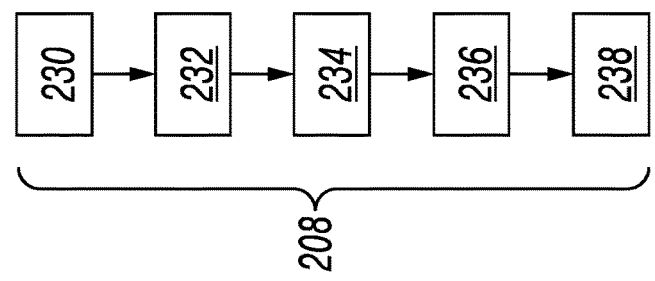
FIGS. 5B & 5C are a first and second embodiment of a same operation of the method of FIG. 5A.
Figure 5B:
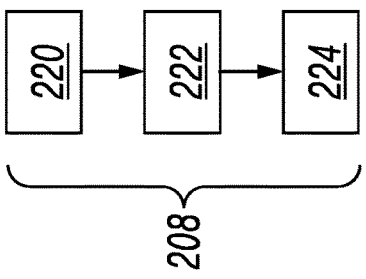
Figure 5A:
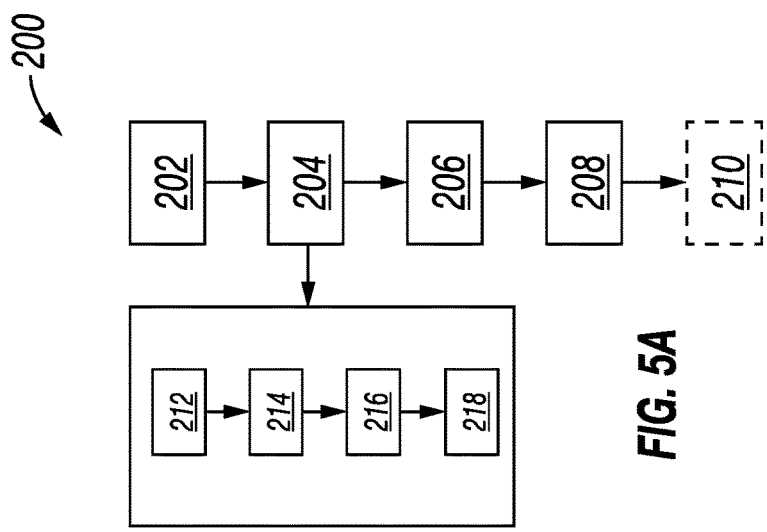
FIG. 5A is a flow diagram of the method for analyzing an earth sample according to an embodiment of the disclosure.

FIG. 5A shows a flow diagram of a method 200 according to the disclosure performed with any cuttings analysis assembly, such as the ones disclosed on FIGS. 1 & 3. FIGS. 5B and 5C show a flow diagram of further embodiments of the method 200.

The method first includes collecting an earth sample (block 202), ie either a core sample or drill cuttings, the earth sample being associated with a depth of the borehole; and performing a Fourier Transform InfraRed (FTIR) spectrometry measurement on the earth sample (block 204) in order to obtain a measured absorbance spectrum as the one of FIG. 4. The method then comprises analyzing the measured spectrum and obtaining from the analyzed measured spectrum a reconstructed spectrum corresponding to a combination of a plurality of standard spectra representative of elements contained in the earth sample (block 206) and detecting a tar layer in the geological formation based on a spectrum representative of the measured spectrum and the mineral reconstructed spectrum (block 208). The method may comprise optionally taking a drilling decision based on the tar layer detection (block 210), such as stopping the drilling or executing a sidetrack to avoid the tar.

Block 204 may in particular comprise optionally preparing the earth sample for the measurement, as explained hereinabove (block 212), and then irradiating the (prepared) sample with infrared energy (block 214) and measuring a spectrum representative of the infrared energy absorbed by the sample (block 216). Depending of the analysis device 55 used, the spectrum representative of the infrared energy absorbed may be obtained from energy transmitted by the sample or diffusely reflected by the sample (if the FTIR spectrometer is a DRIFTS spectrometer).

Block 206 may also comprise analyzing the measured spectrum in order to obtain a total reconstructed spectrum corresponding to a combination of a plurality of standard spectra comprising standard spectra representative of minerals of the earth and of organic matter (such as kerogen) (block 218). It is indeed known in the art to analyze an absorbance spectrum by doing a regression analysis against a plurality of standard spectra, each standard spectrum being representative of at least one element that may be found on earth, such as minerals, kerogen, etc. as explained in US application US20130046469 of the Applicants. For instance, a total reconstructed spectrum may be calculated as being a combination of three standard spectra S1, S2, S3, respectively associated with coefficient a1, a2, a3, and then the total reconstructed spectra will be: S=a1*S1+a2*S2+a3*S3. The regression analysis may be performed by any appropriate way. It enables to determine the composition of the earth sample and generally the mineralogy and TOC (total organic content) of such sample. It may be performed by the calculator 51. The database may for instance store the standard spectra. The total reconstructed spectrum is generally matches very closely the measured spectrum.

At block 206, a mineral reconstructed spectrum may be obtained from the total reconstructed spectrum. The mineral spectrum is the portion of the total reconstructed spectrum due to minerals only. Taking into account the above example of the total reconstructed spectrum S and of the spectrum S3 is a standard spectrum representative of organic matter while S1 and S2 are representative of minerals, the mineral reconstructed spectrum will be S'=a1*S1+a2*S2. The mineral reconstructed spectrum does not match the measured spectrum as part of the elements of the earth sample are not taken into account in this spectrum.

Figure 6:
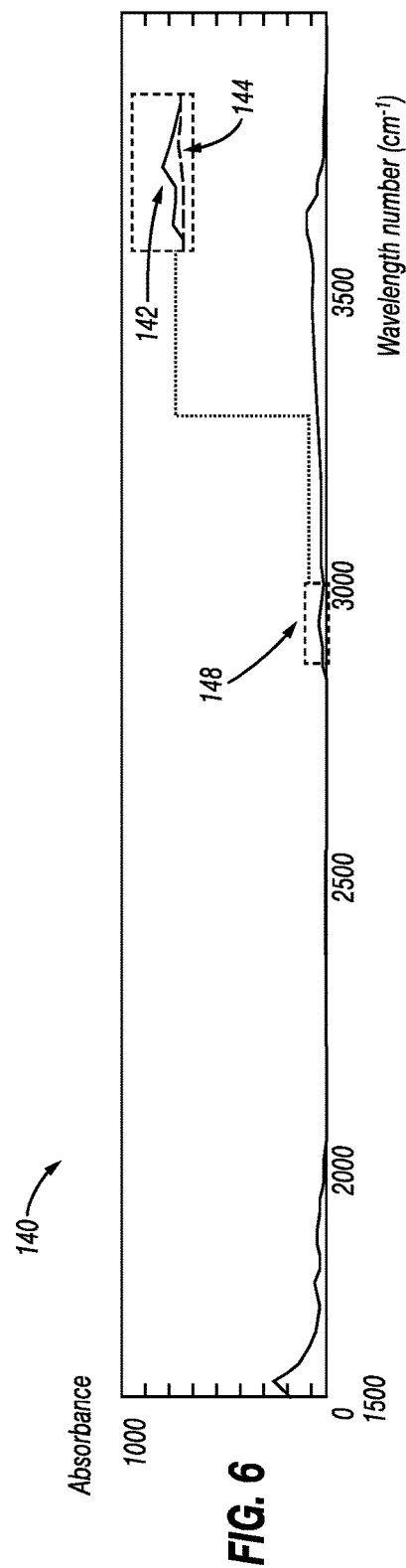
FIG. 6 is a plot of a spectrogram containing a total reconstructed spectrum and a mineral reconstructed spectrum obtained via the method of FIG. 5A based on the measured spectrum of FIG. 4.
Figure 8:
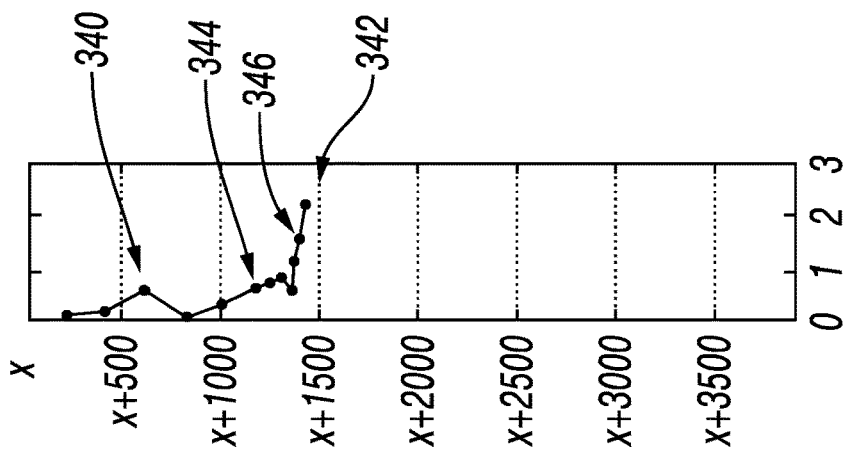
FIG. 8 is a plot of a ratio obtained through the method of FIG. 5C versus depth in the well from which the earth samples analyzed on spectrograms of FIG. 7A-7C are extracted.

For instance, as can be seen on FIG. 6 showing a spectrogram 140 comprising the total reconstructed spectrum 142 and the mineral reconstructed spectrum 144 derived from the measured spectrum 132, there are discrepancies between the total reconstructed spectrum and mineral reconstructed spectrum in 1 wavelength zone 148, in view of the fact that part of the measured spectrum 132 is due to the presence of organic matter in the earth sample.

At block 208, the tar layer is detected, the tar detection including a comparison of the total and/or mineral reconstructed spectrum 144 with the measured spectrum 132 in one or several wavelength zones. A "wavelength zone" may be defined in relationship with the wavelengths or with any indicator depending only on the wavelength, such as the wavelength number.

In a first embodiment, the detection comprises, at block 220, substracting the total reconstructed spectrum 142 from the measured spectrum and to derive, at block 222, an indicator of the absorbance of the resulting spectrum in a wavelength zone having a wavelength number between 1500 and 1700 $cm^{-1}$, in particular between 1600 and 1650 $cm^{-1}$. The indicator may be derived by measuring the area under the resulting spectrum in the said wavelength zone. It includes at block 224 comparing the value of the indicator with a threshold value, such as 0 or a value close to 0.

Indeed, it has been discovered that above tar, the formation may include a signal in this wavelength zone, due to volatile compounds of tar such as double bonds elements C=C or C=O that have escaped from the tar. These compounds are generally not present at abnormally high concentrations in the formation when there is no tar layer and have an absorbance in this wavelength zone.

It has to be noted that for performing the tar detection according to the first embodiment of the disclosure, there is no need to calculate the mineral reconstructed spectrum at block 206.

In a second embodiment, the tar detection comprises, at block 230, subtracting the mineral reconstructed spectrum 142 from the measured spectrum 132 and to derive, at block 232, a first indicator accounting for the absorbance of the resulting spectrum in a first wavelength zone having a wavelength number between 1500 and 1700 $cm^{-1}$, in particular between 1600 and 1650 $cm^{-1}$ and at block 234 a second indicator of the absorbance of the resulting spectrum in a second wavelength zone having a wavelength number between 2800 and 3100 cm$^{-1}$, in particular between 2800 and 3000 cm$^{-1}$. As explained above, the first and second indicators may be obtained by measuring the area under the resulting spectrum.

At block 230, instead of subtracting the mineral reconstructed spectrum from the measured spectrum in the first wavelength zone, the total reconstructed spectrum may be subtracted as explained in reference to the first embodiment. In this embodiment, the mineral reconstructed signal may be subtracted from the measured signal even though the organic matter has a signal in the first wavelength zone because the influence of organic matter may be accounted for by looking at the second wavelength zone.

At block 236, the tar detection comprises building a ratio of the first indicator and a coefficient depending on the second indicator, for instance a ratio of the first and second indicator or a ratio of the first and a linear combination, such as sum, of first and second indicator. This ratio may be compared with a threshold value, such as zero but also with the same ratio calculated for an earth sample taken at a different depth at block 238. This comparison may give extra indication on the location of the tar layer, as the value of the ratio increases when the tar layer approaches. When tar layer is encountered, the value of the ratio decreases at once as the organic content in the second wavelength zone increases greatly.

The method according to the disclosure then enables to detect the tar layer ahead of the bit. FIGS. 7A, 7B and 7C shows spectrograms 300, 310, 320 of a formation including a tar layer, respectively taken 296 ft above the tar layer, 56 ft above the tar layer and at the tar layer. When the tar layer is far deeper in the formation, there is no discrepancies between the measured spectrum 302 and the mineral reconstructed spectrum 304 and then no trace of tar is visible even in the first and second wavelength zones 306 and 308 (FIG. 7A). However, when the tar layer approaches, the signal due to organic matter that are not taken into account in the mineral standard spectra increases in the first wavelength zone 316 (visible through discrepancies between measured spectrum 312 and mineral reconstructed spectrum 314) while the signal due to organic matter in the second wavelength zone 318 remains low (FIG. 0.7B). If such a pattern is observed at several depths close to one another, it will help detecting that a tar layer is ahead of the bit. When drilling through the tar layer, the discrepancies between measured spectrum 322 and mineral reconstructed spectrum 324 increase in first and in particular second zone (FIG. 7C).

Detection is enabled with equivalent efficiency by comparing the measured and total reconstructed spectrum in the first wavelength zone while comparing the measured spectrum to the mineral reconstructed spectrum in the second wavelength zone.

As can be seen on FIG. 7A-7C, when using the method according to the disclosure and calculating the tar ratio as described hereinabove, the tar ratio 340 (here first indicator on second indicator) may be plotted against depth. The ratio evolution may give an extra-information concerning the proximity of the tar layer. Indeed, the tar layer 342 is situated at a previously known depth. At this depth, as already explained, the tar ratio decreases. However, it is clear that before reaching the tar layer, the ratio increases first with a first slope and then with a greater slope which may help detect how close the tar layer is. When the analysis is performed during drilling, it may enable to take a drilling decision before reaching the tar layer, such as stopping or re-routing the drilling.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The disclosure relates generally to a method for analyzing at least an earth sample of a geological formation, comprising:

Performing a Fourier Transform InfraRed (FTIR) spectrometry measurement on an earth sample collected in the formation by:
Irradiating the sample with infrared energy
Measuring a spectrum representative of the infrared energy absorbed by the cuttings,
Analyzing the measured spectrum and obtaining from the analyzed measured spectrum a reconstructed spectrum corresponding to a combination of a plurality of standard spectra representative of elements contained in the earth sample,
Based on the measured spectrum and on the reconstructed spectrum, detecting a tar layer in the geological formation.

The FTIR spectrometry measurement may be a DRIFTS measurement.

The method may be performed during drilling. The earth sample may comprise drill cuttings, collected during the drilling of a borehole in the formation. It may also comprise core samples collected during drilling or not.

The reconstructed spectrum used in the detection may be a total reconstructed spectrum corresponding to a combination of a plurality of standard spectra representative of minerals of the earth and organic matter contained in the earth sample. Alternatively or additionally, it may be a mineral reconstructed spectrum corresponding to a combination of a plurality of standard spectra representative of minerals of the earth contained in the earth sample. In the latter case, obtaining the mineral reconstructed spectrum may include selecting a portion of the total reconstructed spectrum due to the standard spectra representative of minerals of the earth.

In a first embodiment, detecting the tar layer may comprise comparing the measured spectrum and the (total or mineral) reconstructed spectrum in a wavelength zone situated between 1500 and 1700 cm$^{-1}$, for instance between 1600 and 1650 cm$^{-1}$. Comparing the measured spectrum and the reconstructed spectrum may comprise subtracting the reconstructed spectrum from the measured spectrum to obtain a resulting spectrum. Detecting the tar layer may also comprise deriving from the comparison an indicator accounting for the absorbance of the resulting spectrum in the wavelength zone and comparing the indicator to a predetermined threshold value.

In a second embodiment, the wavelength zone indicated above is a first wavelength zone, and the method further comprises comparing the measured spectrum and the mineral reconstructed spectrum in a second wavelength zone situated between 2800 cm$^{-1}$ and 3100 cm$^{-1}$, for instance between 2800 cm$^{-1}$ and 3000 cm$^{-1}$. In the second embodiment, the indicator indicated above is a first indicator, and the method may further comprise comparing the measured spectrum and the mineral reconstructed spectrum in a second wavelength zone situated between 2800 cm$^{-1}$ and 3100 cm$^{-1}$ and deriving from the comparison a second indicator. Comparing the measured spectrum and the mineral reconstructed spectrum may comprise subtracting the mineral reconstructed spectrum from the measured spectrum.

The method according to the second embodiment may include deriving a ratio of the first indicator and a coefficient depending on the second indicator (for instance a linear combination of first and second indicators or the second indicator). It may include comparing the ratio to a predetermined threshold value or comparing the values of the ratio derived for several earth samples associated respectively to several depths (when the method is applied to several earth samples). The ratio may also be plotted against as a function of depth.

The earth sample is associated with a predetermined depth and detecting the tar layer may comprise detecting the tar layer between 0 and 200 ft below the predetermined depth.

The disclosure also generally relates to a system for analyzing an earth sample of a geological formation comprising:
a Fourier Transform InfraRed (FTIR) spectrometry measurement apparatus for:
irradiating an earth sample with infrared energy
Measuring a spectrum representative of the infrared energy absorbed by the earth sample,
A calculator for:
Analyzing the measured spectrum and obtaining from the analyzed measured spectrum a reconstructed spectrum corresponding to a combination of a plurality of standard spectra representative of elements contained in the earth sample,
Based the measured spectrum and on the reconstructed spectrum, detecting a tar layer in the geological formation The disclosure also generally relates to a computer program, comprising machine-readable instructions for:
Receive a measured spectrum obtained from a Fourier Transform InfraRed (FTIR) spectrometry measurement on an earth sample of a geological formation,
Analyzing the measured spectrum and obtaining from the analyzed measured spectrum a reconstructed spectrum corresponding to a combination of a plurality of standard spectra representative of elements contained in the earth sample,
Based on the measured spectrum and the reconstructed spectrum, detecting a tar layer in the geological formation.

The invention claimed is:

1. Method for analyzing at least an earth sample of a geological formation, comprising:
Performing a Fourier Transform InfraRed (FTIR) spectrometry measurement on an earth sample collected in the formation by:
Irradiating the sample with infrared energy
Measuring a spectrum representative of the infrared energy absorbed by the sample,
Analyzing the measured spectrum and obtaining from the analyzed measured spectrum a reconstructed spectrum corresponding to a combination of a plurality of standard spectra representative of elements contained in the earth sample,
comparing the measured spectrum and the reconstructed spectrum in at least a wavelength zone situated between 1500 and 1700 $cm^{-1}$ wherein comparing the measured spectrum and the reconstructed spectrum comprise subtracting the reconstructed spectrum from the measured spectrum to obtain a resulting spectrum, and
deriving from the comparison an indicator accounting for the absorbance of the resulting spectrum in the wavelength zone,
Based at least partially on the indicator, detecting a tar layer in the geological formation, wherein the earth sample is taken in a layer situated above the tar layer.

2. The method of claim 1, wherein the FTIR spectrometry measurement is a DRIFTS measurement.

3. The method of claim 1, wherein the earth sample comprise drill cuttings, collected during the drilling of a borehole in the formation.

4. The method of claim 1, wherein the reconstructed spectrum is a total reconstructed spectrum corresponding to a combination of a plurality of standard spectra representative of minerals of the earth and organic matter contained in the earth sample.

5. The method of claim 1, wherein the reconstructed spectrum is a mineral reconstructed spectrum, corresponding to a combination of a plurality of standard spectra representative of minerals of the earth contained in the earth sample.

6. The method of claim 1, wherein obtaining the mineral reconstructed spectrum includes selecting a portion of the total reconstructed spectrum, corresponding to a combination of a plurality of standard spectra representative of minerals of the earth and organic matter contained in the earth sample, due to the standard spectra representative of minerals.

7. The method of claim 1, wherein the wavelength zone extends between 1600 and 1650 $cm^{-1}$.

8. The method of claim 1, comprising comparing the indicator to a predetermined threshold value.

9. The method of claim 1, wherein the wavelength zone is a first wavelength zone, further comprising comparing the measured spectrum and a mineral reconstructed spectrum in a second wavelength zone situated between 2800 $cm^{-1}$ and 3100 $cm^{-1}$, wherein the mineral reconstructed spectrum corresponds to a combination of a plurality of standard spectra representative of minerals of the earth contained in the earth sample.

10. The method of claim 9, wherein the second wavelength zone extends between 2800 and 3000 $cm^{-1}$.

11. The method of claim 1, wherein the wavelength zone is a first wavelength zone and the indicator is a first indicator, further comprising comparing the measured spectrum and the mineral reconstructed spectrum in a second wavelength zone situated between 2800 $cm^{-1}$ and 3100 $cm^{-1}$ and deriving from the comparison a second indicator, wherein the mineral reconstructed spectrum corresponds to a combination of a plurality of standard spectra representative of minerals of the earth contained in the earth sample.

12. The method of claim 11, comprising deriving a ratio of the first indicator and a coefficient depending on the second indicator and comparing the ratio to a predetermined threshold value.

13. The method of claim 11, wherein each earth sample is associated with a predetermined depth and the method comprises deriving a ratio of the first indicator and a coefficient depending on the second indicator and comparing the values of the ratio derived for several earth samples associated respectively to several depths.

14. The method of claim 13, comprising plotting the ratio as a function of depth.

15. The method of claim 1, wherein the earth sample is associated with a predetermined depth and detecting the tar layer comprise detecting the tar layer between 0 and 200 ft below the predetermined depth.

16. A system for analyzing an earth sample of a geological formation comprising:
- a Fourier Transform InfraRed (FTIR) spectrometry measurement apparatus for:
  - irradiating an earth sample with infrared energy
  - Measuring a spectrum representative of the infrared energy absorbed by the earth sample,
- A calculator for:
  - Analyzing the measured spectrum and obtaining from the analyzed measured spectrum a reconstructed spectrum corresponding to a combination of a plurality of standard spectra representative of elements contained in the earth sample,
  - comparing the measured spectrum and the reconstructed spectrum in at least a wavelength zone situated between 1500 and 1700 $cm^{-1}$ wherein comparing the measured spectrum and the reconstructed spectrum comprise subtracting the reconstructed spectrum from the measured spectrum to obtain a resulting spectrum, and deriving from the comparison an indicator accounting for the absorbance of the resulting spectrum in the wavelength zone,
  - Based at least partially on the indicator, detecting a tar layer in the geological formation, wherein the earth sample is taken in a layer situated above the tar layer.

17. A computer program, comprising machine-readable instructions for:
- Receive a measured spectrum obtained from a Fourier Transform InfraRed (FTIR) spectrometry measurement on an earth sample of a geological formation,
- Analyzing the measured spectrum and obtaining from the analyzed measured spectrum a reconstructed spectrum corresponding to a combination of a plurality of standard spectra representative of elements contained in the earth sample,
- comparing the measured spectrum and the reconstructed spectrum in at least a wavelength zone situated between 1500 and 1700 $cm^{-1}$, wherein comparing the measured spectrum and the reconstructed spectrum comprise subtracting the reconstructed spectrum from the measured spectrum to obtain a resulting spectrum, and deriving from the comparison an indicator accounting for the absorbance of the resulting spectrum in the wavelength zone,
- Based at least partially on the indicator, detecting a tar layer in the geological formation, wherein the earth sample is taken in a layer situated above the tar layer.

* * * * *